United States Patent
Waters

[11] 3,935,073
[45] Jan. 27, 1976

[54] METHOD FOR DETECTING BACTERIA
[75] Inventor: John R. Waters, Towson, Md.
[73] Assignee: Johnston Laboratories, Inc., Cockeysville, Md.
[22] Filed: Sept. 22, 1971
[21] Appl. No.: 182,812

Related U.S. Application Data
[60] Division of Ser. No. 30,675, April 22, 1970, Pat. No. 3,676,679, which is a continuation-in-part of Ser. No. 770,484, Oct. 25, 1968, abandoned.

[52] U.S. Cl............. 195/103.5 R; 195/127; 195/100
[51] Int. Cl............................................... C12k 1/00
[58] Field of Search ........ 195/103.5 R; 260/83.6 FT

[56] References Cited
UNITED STATES PATENTS
2,914,447  11/1959  Levin .............................. 195/103.5
3,657,073  4/1972  Burton ..................... 195/103.5 R X OTHER PUBLICATIONS
Nuclear Science Abstracts 19: 11247, (1965).
Id., 22: 10554, (1968–March).
Id., 19: 38, (1965).
Id., 20: 16371, (1966).
Id., 21: 8226, (1967–March).
Id., 16: 25428, (1962).

Primary Examiner—Alvin E. Tanenholtz

[57] ABSTRACT

A sample of material such as blood, urine, spinal fluid, or the like to be tested for the presence of biological activity is placed into a sterile container together with a suitable growth medium which includes a $C^{14}$ carbon containing carbon source (such as $C^{14}$ substituted glucose) which is fermentable to produce gaseous $C^{14}O_2$. An incubator is provided for exposing the container and its contents to conditions conducive to growth. After a suitable incubation period, a portion of the gaseous atmosphere in the container is withdrawn and analyzed in gaseous form in an ionization chamber for the presence of radioactivity. Valve and conduit means are provided for analyzing a number of samples sequentially.

9 Claims, 4 Drawing Figures

METHOD FOR DETECTING BACTERIA

RELATED APPLICATIONS

This is a division of application Serial No. 30.675, filed Apr. 22, 1970 now U.S. Pat. No. 3,676,679 which is a continuation-in-part of application Serial No. 770,484, filed Oct. 25, 1968 now abandoned.

DESCRIPTION OF INVENTION:

The present invention relates to a method and apparatus for detecting biological activity and particularly for making rapid analyses of materials in which the presence of microorganisms, or the like, is suspected through the use of a growth medium containing radioactivity which is fermentable to produce a radioactive gaseous product.

When, for example, bacteria are cultured in a suitable medium including a fermentable carbon source such as glucose, the source may be broken down to form $CO_2$ during the growth of the bacteria. If the growth medium is alkaline, the $CO_2$ will generally be absorbed to form carbonates or bicarbonates. However, if the starting medium is acidic (or slightly alkaline or neutral so that a slight amount of $CO_2$ absorption will convert the same to acidic conditions), gaseous $CO_2$ will be evolved into the atmosphere above the solution.

If the medium includes a carbon source prepared from radioactive carbon having an atomic weight of 14 ($C^{14}$) rather than normal carbon having an atomic weight of 12, any $CO_2$ liberated will include radioactive $C^{14}O_2$. The radioactivity of the $C^{14}O_2$, which is the result of the beta decay of the $C^{14}$, can be measured. This radioactivity will be generally related to the amount of $CO_2$ generated and thus can be used to measure bacterial presence and growth in the medium.

In the past, the principal method for measuring the radioactivity of the $C^{14}O_2$ liberated has been to collect the $CO_2$ on a filter paper soaked in an alkaline solution. The filter paper, thus containing a radioactive carbonate or bicarbonate in liquid form, is then processed and analyzed for radioactivity in a liquid scintillation counter. This method for determining bacteriological presence and growth by the radioactivity of the $CO_2$ evolved from the medium is slow and laborious.

In hospital work, the early detection of bacteria in body fluids is of paramount importance. It has been a well recognized practice to place blood or urine specimens or the like in an appropriate growth medium on a Petri dish and make visual observations of the bacteriological growth. While this method is also slow and laborious, it does facilitate the final identification of the bacteria. Manifestly, in each method, all samples, whether positive or negative for bacteria, had to be subjected to extensive procedures.

In many cases, proper diagnosis and treatment of diseases would be facilitated if the absence of certain bacteria could be confirmed simply and quickly. Further, if such negative samples could be identified and discarded without extensive processing, much laboratory effort would be eliminated. The latter is also true if the presence of a certain species or at least of a certain group of bacteria could be established rapidly.

The method of the instant invention operates to provide a quick determination of the general presence or absence of most medically significant bacteria in a given sample. Also, the invention provides a quick determination of the presence or absence of a given species or group of bacteria. Further, the invention is adapted to provide automatic analyses, thereby to free laboratory personnel for other activities. In addition, the present invention facilitates the performance of a plurality of individual analyses essentially simultaneously by a single technician.

The novel advantages are achieved through the use of a method which comprises, first, the placing of a sample of material to be tested into a container together with a growth medium including a $C^{14}$ carbon containing carbon source which is metabolizable or fermentable to produce gaseous carbon dioxide. Thereafter, the container having the medium with the sample therein is incubated under conditions conducive to the occurrence of normal metabolic processes for a period of time sufficient to cause production of gaseous carbon dioxide by the fermentation of the carbon source if bacteria are present in the original sample. At least a portion of the gaseous atmosphere from within the container above the medium is then removed. Finally, the radioactivity of the removed portion of gas is measured while the portion remains gasiform to thereby rapidly determine whether or not certain species or groups were present in the original sample. While the method of the invention is not so limited, it is particularly adapted for the detection of medically significant bacteria.

The invention also includes apparatus which operates to achieve the various desirable advantages set forth above. This apparatus includes a container adapted for receiving a sample of material to be analyzed for biological activity together with a growth medium including a $C^{14}$ carbon containing carbon source which is fermentable to produce carbon dioxide. Means are provided for exposing the container and thereby the medium and the sample to conditions conducive to the occurrence of normal metabolic processes. Also provided are radioactivity measuring means operable to measure the radioactivity of a quantity of gas. The container and the radioactivity measuring means are intercommunicated by conduit means and a valve is provided for normally blocking the conduit. The valve is operable to periodically unblock the conduit to permit at least a portion of the gaseous atmosphere in the container to flow into the radioactivity measuring means.

Further, and in another aspect, the invention provides an apparatus for rapidly and sequentially analyzing a plurality of materials for biological activity by measuring the radioactivity of gaseous portions removed, after incubation, from individual containers which originally contained individual samples of the materials to be analyzed together with a growth medium including a $C^{14}$ containing carbon source fermentable to produce carbon dioxide. The apparatus comprises, for these purposes, a conduit segment for each of the containers adapted for connection thereto and a radioactivity measuring device including an ionization chamber operable to facilitate the measurement of the radioactive decay of the $C^{14}$ in $C^{14}O_2$ which is present in gaseous form within the chamber, said chamber having an inlet conduit. The device also includes means operably coupled to the chamber for measuring the electric current produced therein by said decay. Also provided are valve means connected to the conduit segments and the inlet conduit, the valve means being operable to selectively intercommunicate the inlet conduit with any one of the conduit segments individually to permit flow of a gaseous portion from the corresponding container into the chamber. Suction means are coupled to the chamber to flush the chamber after the radioactivity of a portion has been measured.

Figures 1, 2:
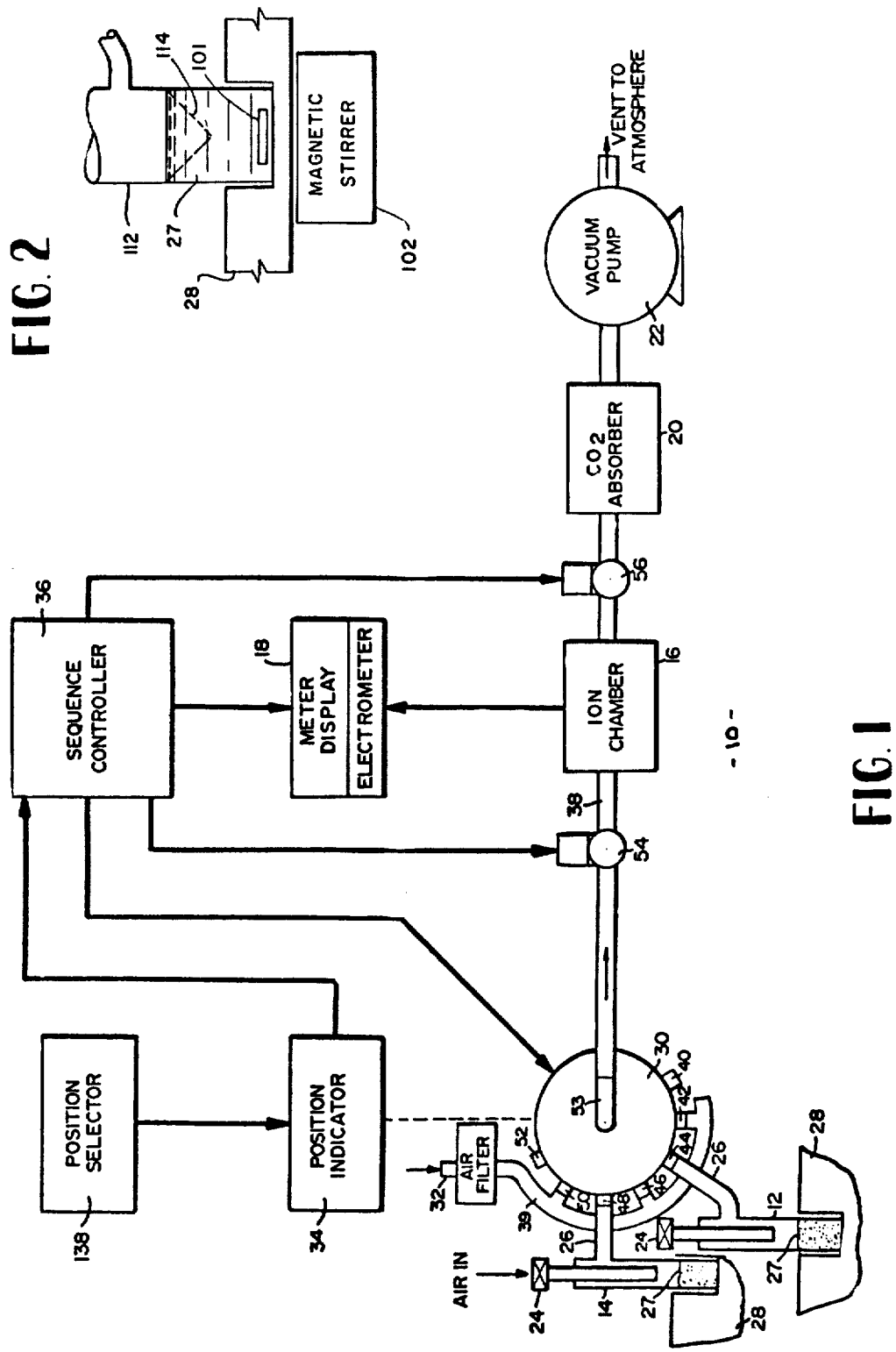
FIG. 1 is a schematic diagram of a biological detector constructed in accordance with the concepts and principles of the instant invention.
FIG. 2 is a detail drawing depicting a preferred means of achieving agitation of the culture medium.

A detector apparatus embodying the principles and concepts of the invention is broadly designated in FIG. 1 by the numeral 10. Apparatus 10 is particularly useful, for example, in providing early detection of the general presence of most medically significant bacteria in materials such as blood, urine, spinal fluid, water samples and the like. The presence of such bacteria is readily detected by measuring the amount of $C^{14}O_2$ generated when a material to be analyzed is placed into a growth medium including a $C^{14}$ carbon containing source (such as $C^{14}$ substituted glucose) which is metabolized or fermented to produce $C^{14}O_2$ and the medium with the sample therein is thereafter incubated. Manifestly, the presence of radioactivity in the atmosphere above the growth medium is an indication of the presence of microorganisms in the original sample of material. It should be noted that the term ferment as employed herein embraces metabolic processes generally.

A sample to be analyzed, such as blood or urine or the like, is placed into sterile culture container 12 or 14 together with a growth medium which preferably includes $C^{14}$ glucose (all carbon atoms replaced by $C^{14}$) and incubated. At suitable intervals, at least a portion of the gaseous atmosphere within the culture chamber 12 or 14 is transferred to a radioactivity measuring means which includes an ionization chamber 16. The electric current produced within chamber 16 by radioactive decay of $C^{14}$ in the gas is measured and displayed on a meter 18 which may include provision for simultaneous recording on an analog recorder (not shown). After the measurement has been made, chamber 16 may be flushed with clean air to sweep residual radioactive $C^{14}O_2$ into an absorber 20. Thereafter, chamber 16 preferably is evacuated by vacuum pump 22 to make sure that all radioactivity is removed from chamber 16 so that the next reading will not be affected.

Apparatus 10 may be used, for example, to detect the presence of bacteria generally rather than to detect a given species. A growth medium which includes $C^{14}$ glucose is preferred and $C^{14}$ glucose constitutes a practical general purpose carbon source. However, it is to be understood that in some instances a given medium may be specific for a given species or at least for a known group and in those instances, the present invention may be utilized to detect the presence or absence of such species or members of such group. While glucose is the preferred medium because it is generally fermentable to form gaseous $CO_2$ by nearly all medically significant bacteria, it is to be appreciated that not all bacteria act on glucose to form gaseous $CO_2$. Some bacteria, for example *Pseudomonas aeruginosa*, *Shigella flexneri*, and *Salmonella typhi*, are listed, in standard works such as Bergey's Manual of DETERMINATIVE BACTERIOLOGY; as not producing $CO_2$ from glucose. This has been found to be at least technically incorrect since the small amounts of $CO_2$ produced, while escaping detection by conventional analyses, are readily detectable by the method of the present invention. However, should a strain or class of bacteria be studied that does not produce $CO_2$ from glucose, some other carbohydrate such as xylose or maltose, can be used to test for such microorganisms. The only necessity being that the carbohydrate includes $C^{14}$ and that it is fermentable by the species or group of interest to form gaseous $C^{14}O_2$.

Standard nutrient mediums operable in this invention generally will contain water, a suitable $C^{14}$ substituted carbohydrate ($C^{14}$ glucose), a nitrogen source, calcium, magnesium, potassium, phosphate, sulfate, and minor elements. The medium may also include a buffer for pH adjustment and maintenance.

While, as stated above, $C^{14}$ glucose is the preferred carbon source, other $C^{14}$ substituted sugars, such as sucrose, fructose, xylose, maltose, lactose and the like, as well as mixtures of such sugars, may be employed in the practice of this invention, generally for more specific determinations. The invention also contemplates the use of fermentation mediums containing $C^{14}$ carbon substituted carbohydrates generally including starches, dextrins, and the like as well as sugars. Such radioactive materials are well known to those skilled in this art. As employed herein, the terms "sugar," "starch," and the like embrace not only such materials, per se, but their obvious equivalents, such as, for example, molasses and the like. For maximum sensitivity, all of the carbon atoms in the carbon source are preferably replaced by $C^{14}$ carbon although this is not absolutely necessary so long as the $C^{14}$ is substituted in the correct position in the carbohydrate molecule so that it is liberated as $C^{14}O_2$. In this regard, it should be noted, as is well understood by those skilled in the art, that the $C^{14}$ cannot be substituted at random in the molecule, but its position must be selected carefully.

The carbohydrates are employed in the fermentation medium in amounts of at least about 0.0001% weight. Desirably the medium will contain from about 0.0003% to about 0.001% carbohydrate although fermentation mediums containing up to about 20% carbohydrate and above are operable. The $C^{14}$ activity supplied by the carbohydrate can be in the range of from less than 0.1 micro curie to about 10 micro curies or more per 10 ml of medium, although about 0.5 micro curies is preferred. It will be apparent that the precise proportion of carbohydrate employed in the medium will generally be a matter of choice.

The medium also may contain a standard nitrogen source, such as nitrates, nitrites, ammonia, urea, or other assimilable nitrogen source either organic or inorganic. Preferably, at least sufficient nitrogen is present to supply nitrogen for cell growth.

A variety of calcium, potassium, and magnesium salts may be employed in the fermentation medium including the chlorides, sulfates, phosphates and the like. Similarly, phosphate and sulfate ions can be supplied as any of a variety of salts. While salts which supply both the desired anion and cation may be employed (e.g., potassium phosphate, magnesium sulfate) the selection is by no means so limited. Again, such materials are conventional in fermentation mediums and the selection of specific materials as well as their proportion is within the skill of the routineer.

The so-called "minor elements" are commonly understood to include manganese, iron, zinc, cobalt, and possibly others. Trace quantities thereof are preferred, and such quantities are commonly present in the materials used in the preparation of fermentation mediums.

Finally, the medium may contain a buffer to maintain the pH in the desired range. Once more a wide variety of materials may be utilized. Potassium or ammonium phosphates often are employed to maintain the pH of fermentation media.

A particularly preferred type of medium is known as thioglycolate and is a generally used, widely available medium. The composition of thioglycolate without its glucose is as follows:

trypticase 15.0 gms/l
1-cystine 0.5 gms/l
yeast extract 5.0 gms/l
sodium chloride 2.5 gms/l
sodium thioglycolate 0.5 gms/l
resazurin 0.001 gms/l
agar 0.75 gms/l $C^{14}$ carbon containing glucose is added to this composition in accordance with the criteria set forth above to produce the complete preferred growth medium containing radioactivity.

Another acceptable type of medium which is generally available is a brain-heart-infusion broth (BHI) having the following composition in 1 liter of aqueous broth;

infusion from 200 ml of calf's brain
infusion from 250 ml of beef heart
10 gms of peptone gelysate
5 gms of sodium chloride
2.5 gms of disodium phosphate Again, the $C^{14}$ substituted carbohydrate is added to this composition to produce a growth medium containing radioactivity.

At the outset of the process, the fermentation medium is inoculated with a sample of the material to be tested while the pH is maintained between about 6 and about 7 and desirably at about 7. The amount of sample employed may vary widely but often is preferably from about 0.01% to about 10% by volume. After a short delay, any organisms present will grow rapidly followed by a decrease in growth rate. In addition, the rate of fermentation and thereby the rate of evolution of $CO_2$ will vary depending upon such factors as nutrient composition, pH, temperature, proportion of inoculum, and the like.

For effective fermentation for the majority of bacteria, the temperature of the medium with the sample therein is preferably maintained between about 35°C and about 39°C. Some organisms achieve optimum growth at temperature of 20°C or lower while others may exhibit optimum growth at 45°C or higher. This invention may employ any temperature best suited in a given circumstance. Although satisfactory growth can be achieved without agitation, fermentation preferably is carried out with active shaking, stirring, or the like, effective to insure proper evolution of $CO_2$ from the medium. In one preferred embodiment, agitation is provided by stirring to introduce a vortex into the liquid medium. An external stirring apparatus to provide the vortex is desirable and is described more fully hereinafter with reference to FIG. 3.

Most often, interest will be in determining whether a given sample contains aerobic bacteria and, therefore, the atmosphere in the containers generally will be air or oxygen. This invention can be used to detect anerobic bacteria, however, by employing nitrogen or the like as an inert atmosphere and flushing gas. It will be appreciated that light may be provided in the event organisms responsive to light are being investigated.

Turning now more particularly to the mechanical equipment depicted in FIG. 1, the culture containers 12 and 14 preferably will have a total capacity of approximately 50 ml, of which 15–25 ml will be occupied by the culture medium and test sample. The volume of blood or urine or other sample may be, for example, 1–3 ml.

A submicron filter 24 which includes a check valve, is provided for each container 12 and 14 to allow airborne bacteria and other particulate contaminants to be removed from surrounding atmosphere drawn into the containers 12 and 14. An outlet conduit segment 26 generally preceded by an absorptive filter (not shown) is provided for each container 12 and 14 to prevent droplets of culture medium from leaving the culture container. Segments 26 are located well above the culture medium level 27. Containers 12 and 14 are preferably constructed of components suitable to permit sterilization by autoclaving or gas sterilization methods.

Culture containers 12 and 14 with the culture medium and test samples therein are disposed in a thermostatically controlled temperature incubator 28, where the temperature is maintained preferably at 37°C± 2°C to provide optimum conditions for growth.

One gaseous radioactivity detector, such as chamber 16, is used in common with a plurality of culture containers such as containers 12 and 14. In this regard, it should be noted that while only two containers 12 and 14 are shown, at least 10 to 20 are actually preferred for greater efficiency. A sequential gas selector valve 30 is used to connect the detector chamber 16 alternately to a culture container, such as 12 or 14, and then to a source 32 of filtered air for flushing the contents of detector chamber 16. Valve 30 is shown as including a plurality of inlets 40, 42, 44, 46, 48, 50 and 52. In actual practice, however, valve 30 preferably will have as many as 20 to 40 or more inlets. Port means disposed internally of valve 30 are operable selectively to intercommunicate any one of the inlets 40-52 with valve outlet 53. As shown, inlet 44 is coupled with the conduit segment 26 of container 12 and inlet 48 is coupled with the conduit segment 26 of container 14. Inlets 42, 46 and 50 are coupled with a manifold 39 which communicates with filtered air source 32. Inlets 40 and 52 are not coupled as shown. However, it is to be understood that additional containers could be coupled to these inlets. Incubator 28 also includes facilities for handling additional containers.

A pair of solenoid valves 54 and 56 are provided for blocking or unblocking the conduits on either side of chamber 16 as may be required for purging or evacuating chamber 16. A position indicator 34 may provide electrical identification of the position of valve 30. Indicator 34 is actuated by a multiposition switch (not shown) mechanically coupled to valve 30.

Ionization chamber 16 is preferably a conventional type of radioactivity detector similar to that used in the Johnston Laboratories' TRITON Model 755C. Chamber 16 is used to provide an electrical output current corresponding to the amount of radioactivity present therein. The electrical output, which is displayed on meter 18, should preferably correspond to a sensitivity of at least about 12 picocuries of $C^{14}$ per milliliter of air at full-scale or approximately 14 nanocuries of activity in the ion chamber 16. An output for connection to a 10 milivolt full-scale analog recorder may also be provided along with an attenuator which permits recording outputs corresponding to 120 picocuries of $C^{14}$ per milliliter of air at full-scale. Also, other devices capable of measuring radioactivity in a gaseous medium may be utilized. Specifically, this may include such devices as scintillation counters, proportional counters, Geiger counters and ionization chambers operated in the pulsed mode.

The level of radioactivity which must be detected before a culture can be identified as containing biological activity is preset on meter 18 which also may include an electric relay. As will be appreciated by those skilled in the art, ionization chambers such as chamber 16, are preferably preset (or calibrated) by empirical methods prior to their use for analytical purposes. When the preset level is exceeded by the amount of radioactivity in a given portion of gas being analyzed, an indicator light corresponding to the appropriate culture container may be activated and an audible alarm may be sounded. The indication of activity preferably remains actuated until intentionally reset by an operator. In the event of temporary power failure, a battery-powered electronic logic element may be provided to retain the indicator state of each culture container for display upon resuming normal operation. The operation of the entire indicating system preferably is designed so that it may be tested at any time without changing any indicator state.

The sequence of operations which must be performed for each measurement is controlled by a motor driven cam operated programmer 36. Both manual and automatic operating modes may be provided. In the automatic mode, the sequence controller 36 may begin operation, for example, at a selected time interval of 1, 2, 3 or 4 hours after the initiation of the incubation of the sample and the culture medium. Controller 36 causes apparatus 10 to measure sequentially all culture containers seriatim and then return to its standby (initial) position until the selected interval of time again has elapsed after which the cycle is repeated. Manifestly, a series of portions may be removed from each container and analyzed to indicate the amount of biological activity during any given time period. The sequence controller measurement sequence is actuated by a push-button switch, at which time a reading is taken. At the completion of the reading cycle, the sequence controller 36 returns to its standby condition with the sequential selector valve 30 positioned at the selected container. In the manual mode of operation, the sequential selector valve 30 may be automatically positioned at an operator selected container by a position selector 138.

In operation, valve 30 is operated to intercommunicate the conduit segment 26 of any container (12 or 14 or any other container) and the inlet conduit 38 of chamber 16. For this purpose, valve 54 is opened. At least a portion of the gaseous contents of the selected culture container are transferred into ionization chamber 16 whereupon valve 54 is closed. For this purpose, chamber 16 will have been left at least partially evacuated at the end of the previous cycle and this vacuum will provide the impetus for transferring the gaseous contents from the container into the chamber. Thereafter, the current reading in chamber 16 is taken. If the level of radioactivity exceeds the preset limit, the appropriate growth indicator lamp lights and the audible alarm sounds. After the measurement is made, the sequential selector valve 30 is actuated to its next position to intercommunicate inlet conduit 38 and filtered air source 32. Then, valves 54 and 56 are opened and pump 22 is actuated whereby filtered atmospheric air may be sucked through the ionization chamber 16 and its associated conduits to flush any activity present therein and trap it in the carbon dioxide filter 20. Then valve 54 may be closed while valve 56 remains open and pump 22 remains actuated to evacuate chamber 16 to further rid chamber 16 of any residual radioactivity. Thereafter, valve 56 is closed and pump 22 is turned off. This also establishes the vacuum for sucking the next gaseous portion into chamber 16. This cycle is repeated on each container. In this regard, valve 30 operates as a rotary stepping switch connecting one inlet (44 or 48) at a time to outlet 53. Thus, for example, inlet 44 is connected to outlet 53 and the gaseous contents of container 12 are drawn into chamber 16. Thereafter, valve 30 steps one position so that inlet 46 and outlet 53 are intercommunicated. Thus, clean filtered air from source 32 passes through apparatus 10 via manifold 39, inlet 46, outlet 53 and conduit 38 and chamber 16 to purge the latter and all its associated conduits. After purging and evacuation are complete, valve 30 steps to its next position interconnecting inlet 48 and outlet 53, so that the gaseous atmosphere in container 14 may be monitored. If after a suitable incubation period, no radioactivity is detected, it can be concluded that the original sample was negative.

A preferred apparatus for providing agitation of the liquid culture medium is shown in FIG. 2. In FIG. 2, tubular chamber 112 contains liquid culture medium 27. A small magnetic bar 101 is located within chamber 112 and is rotated by magnetic stirring mechanism 102 to provide a vortex 114 in the medium. Stirring mechanism 102 may contain a conventional bar magnet horizontally rotated by a standard A.C. motor. The magnetic field between magnet 101 and the magnet of stirring mechanism 102 causes both to rotate when the magnet of stirrer 102 is rotated by the A.C. motor. Heat block 28 desirably surrounds at least the lower portion of chamber 112 to maintain an appropriate culture temperature. For compact operation, the heat block and stirrer may be combined to provide a single unit.

A great advantage of the technique of this invention of letting the $C^{14}O_2$ evolve in a closed container and then extracting it as a gas to measure its activity is that it is faster than previously known methods and lends itself to automation. Many samples can be incubated in their sealed containers and then inspected sequentially by an automatic instrument. Thus, samples which are negative are rapidly identified and therefore need not be subjected to extensive analyses.

In one form the apparatus of the instant invention includes provision for a plurality of relatively stationary culture containers and a multiposition valve for selectively coupling the containers to the ion chamber. Alternately, the containers can be arranged in an automatic feeder arrangement wherein the containers are brought sequentially past a connector mechanism coupled to the ion chamber. Thus, the gaseous atmosphere would be drawn off of a container and the next container thereafter moved into position. Such second form of the apparatus is shown in FIGS. 3 and 4.

Housing 110 contains an ion chamber 106, electrometer and meter display 118, sequence controller 136, CO₂ absorber 120, vacuum pump 122 and valves 154 and 156 corresponding generally to the apparatus depicted in FIG. 1. Containers 112 and 114 having self-sealing caps are positioned in automatic feeding mechanism 166 which is circular and passes the containers beneath hood 164 sequentially. After each container is brought into position, sterile hypodermic needles 162 and 163 penetrate the cap of the container and gas is drawn from the container through valve 161 and into ion chamber 106 for measurement of its radioactivity.

Figure 4:
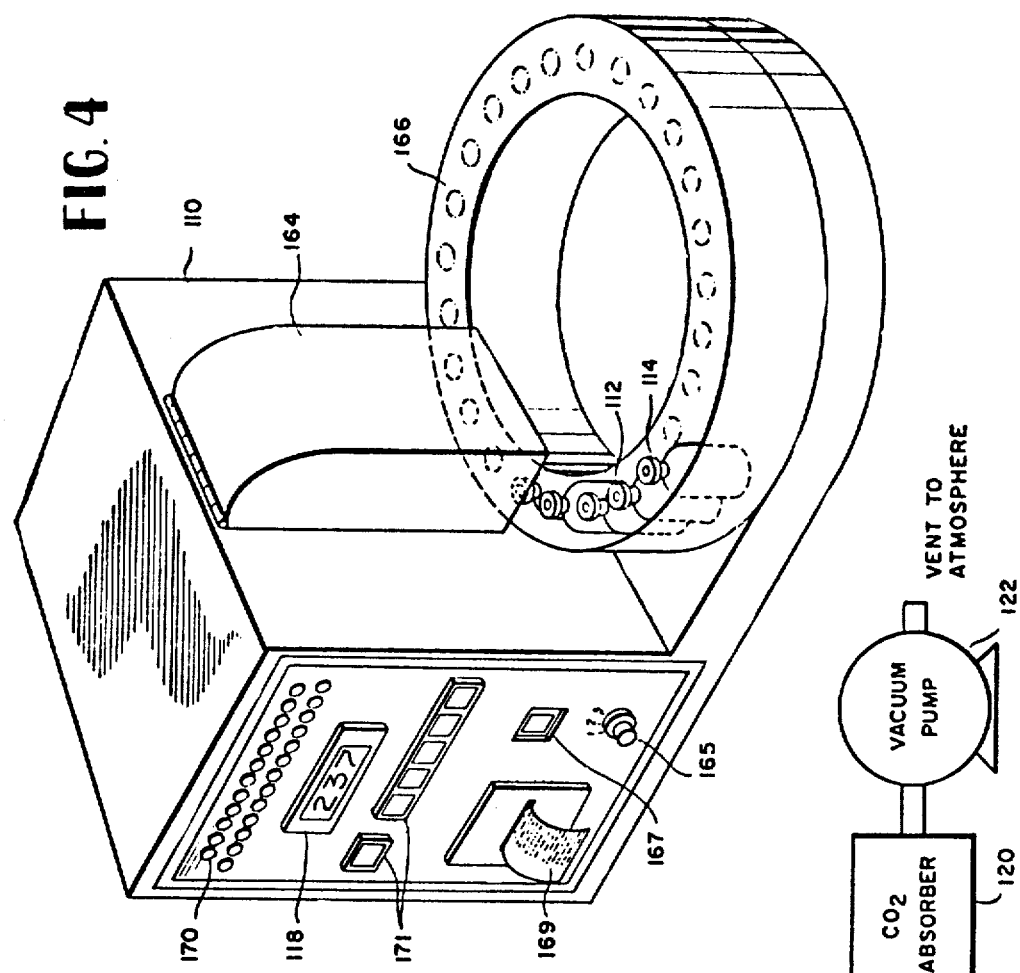
FIGS. 3 and 4 depict another apparatus embodiment of the instant invention.
Figure 3:
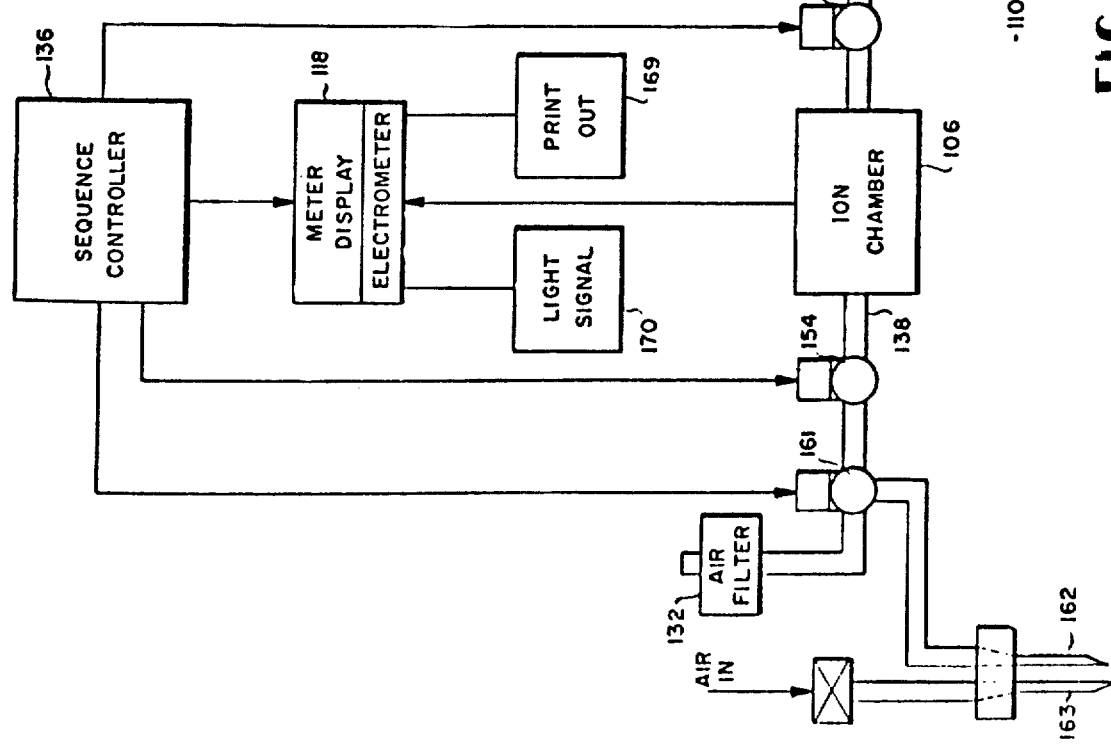

In addition to the basic elements necessary for operation, the apparatus desirably will also have a number of optional features as shown in FIGS. 3 and 4. The position of the container in feeder 166 may be identified such as by number and the machine may be provided with a corresponding number of lights 170. In the event the radioactivity of a sample is above the preset minimum level, the appropriate light will go on and stay on to indicate activity. At the time each container is sampled, the identity of the container is shown at 167 and the activity is displayed on display meter 118. The apparatus may include a print-out component 169 that prints out the sample number and the measured level of activity. Any activity over the predetermined minimum can be automatically "flagged" on the print-out if desired. Switches 171 may be provided for turning the apparatus on, for selection of automatic or manual operation, and the like.

Apparatus 110 also may be provided with a variable control 165 to permit an operator to select any of several desired cycles. After the gaseous atmosphere of the container has been sampled, valve 161 connects the ion chamber 106 with filtered air 132 to allow the ion chamber to be flushed as described with regard to the apparatus of FIG. 1. After the ion chamber has been flushed with air and a vacuum established, the apparatus is in condition to sample the next chamber. The entire sequence of sampling and recording may occur in about 2 minutes.

While the apparatus of FIG. 4 is shown with the automatic feeding mechanism 166 located adjacent housing 110, it should be understood that the apparatus may also be provided in other forms. For example, in order to save space, automatic feeding mechanism may be mounted on top of housing 110 with hypodermic needles 162 and 163 appropriately relocated. Further, this invention also contemplates the positioning of the sample bottles at a location remote from the data recording units. Such positioning, inter alia, permits the sample containers to be shielded by lead or the like in the event that gamma emitting samples are employed.

While the use of the apparatus has been described with respect to the detection of bacteria, the apparatus may be used to detect biological activity broadly including, inter alia, other single cell organisms, enzymes and the like. Variations of the invention described herein will be apparent to those skilled in the art. It is intended, therefore, that the invention be limited only by the scope of the appended claims.

I claim:

1. A method for analyzing a body fluid for the presence of bacteria therein, said method comprising:
    placing a sample of the body fluid into a closed container together with a growth medium containing water including a $C^{14}$ carbon containing carbon source which is fermentable to produce carbon dioxide;
    exposing the medium with the sample therein in said closed container to conditions conducive to the occurrence of normal metabolic processes for a period of time sufficient to cause production of $C^{14}O_2$ by the fermentation of said source;
    thereafter removing at least a portion of the gaseous atmosphere from within the container above the medium and the sample and replacing a portion of the atmosphere in said container; and
    determining the presence of $C^{14}O_2$ in said gaseous atmosphere by measuring the radioactivity of said removed portion of said gaseous atmosphere in radioactivity measuring means while the gaseous atmosphere remains in a gaseous condition; and flushing said radioactivity measuring means with gas to remove the radioactive gaseous atmosphere therefrom.

2. A method as set forth in claim 1 wherein a series of said portions are removed from within the container, the radioactivity of each of said portions being measured while the portions remain in gaseous form to thereby determine the relative presence of $C^{14}O_2$ in said atmosphere in relationship to the amount of time that the sample and the medium have been exposed to fermentation conditions.

3. A method as set forth in claim 1 wherein said measuring is conducted in a measuring zone and a plurality of said analyses are conducted in sequence, the portions from different containers being fed into said zone seriatim and analyzed for radioactivity.

4. A method as set forth in claim 1 wherein said source comprises $C^{14}$ substituted glucose.

5. The method of claim 1 in which a vortex is maintained in the medium in order to promote growth.

6. The method of claim 1 in which the body fluid analyzed is blood.

7. The method of claim 1 in which the medium is subjected to agitation.

8. The method of claim 1 in which the gaseous atmosphere is removed from said container by connecting said container to a partial vacuum.

9. A method for analyzing fluidized materials capable of supporting biological activity for the presence of bacteria therein, said method comprising:
    placing separate samples of said fluidized materials into a plurality of closed sterile containers together with a growth medium containing water including a $C^{14}$ carbon containing carbon source which is fermentable to produce carbon dioxide;
    exposing the medium with the sample in each said closed container to conditions conducive to the occurrence of normal metabolic processes for a period of time sufficient to cause production of $C^{14}O_2$ by the fermentation of said source; thereafter
    removing at least a portion of the gaseous atmosphere from within a container above the medium and the sample and replacing a portion of the atmosphere in said container;
    determining the presence of $C^{14}O_2$ in said gaseous atmosphere by measuring the radioactivity of said removed portion of said gaseous atmosphere in radioactivity measuring means while the gaseous atmosphere remains in a gaseous condition, and
    flushing said radioactivity measuring means with gas to remove the radioactive gaseous atmosphere therefrom; and thereafter removing at least another portion of the gaseous atmosphere from within a container above the medium and the sample and replacing a portion of the atmosphere in said container; and determining the presence of $C^{14}O_2$ in said gaseous atmosphere by measuring the radioactivity of said removed portion of said gaseous atmosphere in radioactivity measuring means while the gaseous atmosphere remains in a gaseous condition, and flushing said radioactivity measuring means with gas to remove the radioactive gaseous atmosphere therefrom.

* * * * *